United States Patent [19]

Bloxom, Jr.

[11] Patent Number: 4,790,811
[45] Date of Patent: Dec. 13, 1988

[54] COLONIC AND INTESTINAL IRRIGATION SYSTEM WITH FLOW INDICATOR

[76] Inventor: I. B. Bloxom, Jr., P.O. Box 357, Wicomico, Va. 23184

[21] Appl. No.: 126,805

[22] Filed: Sep. 24, 1987

Related U.S. Application Data

[60] Continuation-in-part of Ser. No. 858,708, May 2, 1986, Pat. No. 4,698,054, which is a continuation of Ser. No. 707,717, Mar. 4, 1985, abandoned, which is a division of Ser. No. 556,036, Nov. 29, 1983, Pat. No. 4,518,382.

[51] Int. Cl.$^4$ ............................................. A61M 1/00
[52] U.S. Cl. .................................... 604/27; 604/48; 604/73; 604/257; 116/264
[58] Field of Search ............... 116/70, 220, 266, 264, 116/268, 273; 604/27, 29–34, 48, 54, 73, 80, 131, 132, 257, 277

[56] References Cited

U.S. PATENT DOCUMENTS

| | | | |
|---|---|---|---|
| 2,024,967 | 12/1935 | Dierker | 604/30 |
| 2,067,474 | 1/1937 | Carbonara | 33/365 |
| 2,245,653 | 6/1941 | Dierker | 604/35 |
| 3,185,153 | 5/1965 | Leucci | 604/31 |
| 4,497,434 | 2/1985 | Lawless | 116/264 |

Primary Examiner—Stephen C. Pellegrino
Assistant Examiner—J. L. Kruter
Attorney, Agent, or Firm—John Cyril Malloy

[57] ABSTRACT

An apparatus for accomplishing irrigation of the colon and or other intestinal portions through a stoma including establishing a path of fluid flow of irrigating liquid from a supply container through a feeding conduit into a stoma cone or like structure and further including a peristaltic action monitoring device disposed within the path of fluid flow of irrigating fluid. The monitory device is structured to indicate, through the provision of two separate parallel paths of fluid flow, the establishment of peristaltic action in the intestine which tends to reverse the direction of flow of the irrigating liquid from the stoma toward the monitory device and provides proper indication when the flow of irrigating liquid to the intestine or colon should be stopped.

14 Claims, 1 Drawing Sheet

COLONIC AND INTESTINAL IRRIGATION SYSTEM WITH FLOW INDICATOR

BACKGROUND OF THE INVENTION

This is a continuation in part of presently pending U.S. patent application Ser. No. 858,708 filed May 2, 1986 now U.S. Pat. No. 4,698,054 which is a continuation application of then presently pending application Ser. No. 707,717 filed Mar. 4, 1985, now abandoned, which was a divisional application of then copending patent application Ser. No. 556,036 filed on Nov. 29, 1983 which has issued into U.S. Pat. No. 4,518,382.

FIELD OF THE INVENTION

The present invention relates to a system for the controlled irrigating of a stoma or other intestine to the extent that the quantity of irrigating liquid supplied is controlled through an indication of development of sufficient peristaltic action in the intestine wherein the development of such peristaltic action provides a clear indication of sufficient irrigating liquid being supplied thereto to accomplish evacuation. A flow indicator means is provided and structured to indicate the development of even a minimal amount of peristaltic pressure or action in the intestine common to certain persons such as the very old, very young or generally weak patient.

DESCRIPTION OF THE PRIOR ART

Colonic irrigation is a well known medical treatment, not only in the case of conventional enemas through an anus end of the rectum, but also in the case of irrigation through surgically provided openings into other parts of the colon, such as in the case of colostomy patients. In all of these cases the degree of discomfort and length of ordeal is significant. Although varying in particular cases, it is particularly disagreeble for those requiring irrigation directly into the colon through a surgically provided stoma. Such stomas are performed through the end of the shortened colon after the end has been drawn up through the stomach wall and outer skin.

Prior skin irrigating equipment exists to introduce irrigation liquid into the colon of a patient as disclosed for example in U.S. Pat. No. 3,830,235 to Marsan. Such equipment conventonally includes a bag for the irrigating liquid, a tube to convey liquid from the bag to the stoma cone through which the liquid is introduced in the colon, and means to shut off through the tube to the colon. In addition a discharge device to catch the back flow when the cone is removed from the stoma is also provided.

One problem associated with the prior art device of the type set forth above is the inability to effectively determine when sufficient irrigating liquid has been supplied to the stoma to accomplish evacuation thereof. Accordingly, the discomfort associated with colonic of other intestinal irrigation is minimized by detecting the build up of peristaltic action of the intestine in response to the injection of irrigating liquid. Proper termination of the injection of irrigating liquid when there is an indication of sufficient peristaltic action to provide the desirous evacuation minimizes discomfort. Such prompt termination is the further an important advantage in the prevention of an excessively large injection of liquid from suppressing the peristaltic action initiated by the smaller amount of fluid intially injected.

It is also well recognized that depending on the age and general health of the person requiring intestinal irrigation, the resulting development and amount of peristaltic action or "force" developed within the intestine varies from patient to patient. Accordingly, it is particularly important to utilize a monitoring facility which will provide a clear and reliable indication of even a minimal peristaltic action developed within the intestine so that excessively large additional injections of irrigating fluid may be prevented in order not to supress the minimal or "weak" peristaltic action first initiated.

At the same time, such a preferred monitoring device of the types set forth above should also be capable of use with patients having average or greater than average peristaltic force or action normally developed in the colon when sufficiently minimal amounts of irrigating liquid have been introduced thereto.

Based on the above, it should be readily apparent that a preferred monitoring assembly used in combination with an irrigation system of the type set forth herein should be capable of monitoring the development of peristaltic action or force within the intestine in varying degrees or amounts so that the same monitoring assembly can be used with a variety of patients to accomplish the preferred result. Further, the versatility in monitoring assemblies of the type set forth herein are important because if all the monitoring assemblies were structured to be extremely sensitive, the normal patient would commonly have introduced insufficient irrigating liquid to establish sufficient peristaltic action to accomplish evacuation.

SUMMARY OF THE INVENTION

This invention relates to a system for selected and controlled irrigation of the colon or other portions of the intestine to the extent that the quantity of irrigating liquid supplied be sufficient to establish peristaltic action but not excessive to the extent of suppressing initially established peristaltic action or of causing harm to the patient in terms of water intoxication, etc.

Particularly, the system of the present invention incorporates the inclusion of a monitoring facility in the form of a flow indicator mean disposed in fluid communication within a conduit means. A supply container holding and storing irrigating fluid is secured to one end of the conduit means and through relative placement and interconnection therebetween. A gravity flow of the irrigating fluid serves to force travel of the irrigating fluid to the opposite end of the conduit means and at all times through the flow monitoring means. The opposite end of the conduit means relative to the supply container is the provision of an introduction means designed to provide introduction to the receiving end of the colon or intestine such that the irrigating fluid will be efficiently supplied directly thereto.

An important feature of the present invention is the provision of the flow indicator means specifically structured and designed and, as set forth above, disposed in direct fluid communication with the conduit means and the irrigating liquid passing therealong to indicate to the patient, user or other observing personnel the direction of flow of the irrigating liquid through the conduit means.

It is commonly known and well established that upon even an initial development of peristaltic action within the intestine being irrigated, a back flow of irrigating fluid occurs from the intestine back through the conduit means at least to the point of the location of the flow indicator means. Again, due to the structure of the flow indicator means, such back flow will be indicated by a travel of an indicator structure along a designated flow path in a reverse direction than when irrigating fluid is initially supplied to the colon or other intestinal portions.

Even more important is the versatility in both structure and design of the subject flow indicator means through the provision of two parallel flow paths each having correspondingly positioned opposite ends communicating with one another and with an appropriately positioned portion of the conduit means to establish fluid communication therebetween. Therefore, as the irrigating fluid passes from the supply container through a first portion of the conduit means it reaches the flow indicator means and is immediately "separated into each of the two parallel flow paths". If each of the flow paths further include individual indicator elements disposed therein to travel along the length thereof. The indicator elements are specifically dimensioned to flow along the length of the respective flow paths or more specifically conduits or tubes defining such flow paths. In addition, they are also dimensioned relative to the interior dimension of the tubes or flow paths to allow irrigating liquid to pass therebeyond so that it may eventually pass throughout the remainder of the length of the conduit means and reach the introduction means and eventually be introduced into the colon or intestine being irrigated. When such happens, the indicator elements in both of the aforementioned flow paths will be located at a distal end of their respective flow paths clearly indicating that a direction of liquid flow of the irrigating liquid continues from the supply container to the colon through the aforementioned conduit means and flow indicator means.

However, upon the development of even a minimal amount of peristaltic action a resulting back flow of liquid will occur from the intestine, or introduction means through the lower or distal part of the conduit means to the flow indicator means. Once such back pressure reaches both of the flow paths, the respective indicators located therein will begin a reverse direction of travel. More specifically, each of the indicator elements will travel in a direction from the introduction means or colon being irrigated towards the supply container.

An important feature of the present invention will be the specific gravity of the respective elements and their structure so as to detect changes of pressure in the flow paths differently, thereby making the indication of the flow in the first path more rapid than that of the flow in the second flow path, that is, more "sensitive" or responsive to the development of even a minimal amount of peristaltic action and a minimal amount of back flow. Such as particularly important for "weak" patients such as the elderly, very young or patients in generally ill health. Typically, the development of the "weak" peristaltic action, sufficient to accomplish evacuation, may go undetected unless the more sensitive flow detection of the first path is provided with its flow indicator of a specific gravity of about 1. However the flow indicator means of the present invention further includes an additional aforementioned second flow path with accompanying indicator, therein. This second flow path and accompanying indicator element is of a significantly larger specific gravity and is of a larger transverse dimension than the first flow path so as to clearly indicate the development of "normal" peristaltic action or force in the intestine.

Therefore it should be readily apparent that the system of the present invention incorporating the aforementioned monitoring facility allows for sufficient versatility of the system so as to be used with patients which are weak, young or of ill health, and "normal" patients.

The invention accordingly comprises features of construction, a combination of elements and an arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several use of the drawings.

DETAILED DESCRIPTION OF THE PREFERRED EMBODIMENT

Figure 1:
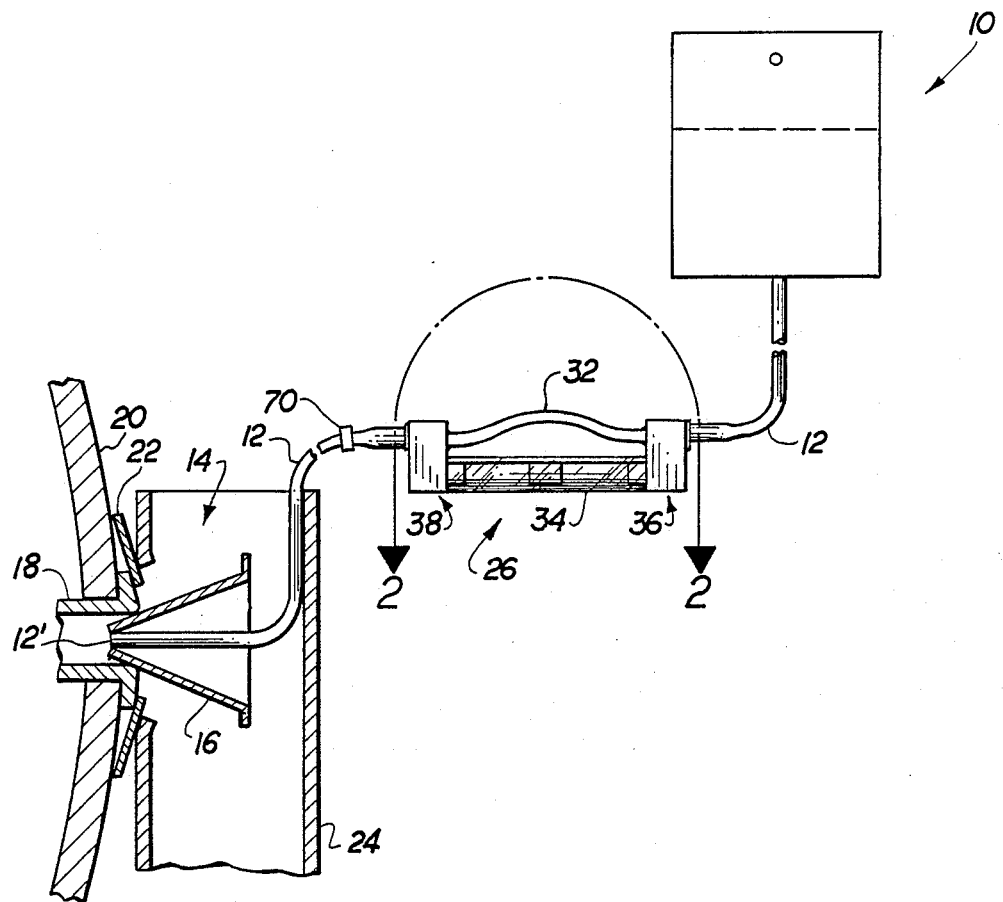
FIG. 1 is a schematic representation in partial cutaway and cross-section showing the system of the present invention incorporating a monitoring facility as part thereof.

As shown in FIGS. 1 through 4 the present invention is directed towards apparatus for controlled intestinal irrigation and comprise a supply container 10 designed to hold irrigating liquid therein and positionable to accomplish gravity flow through conduit means 12. The gravity flow of irrigating liquid travels from the supply container 10 through the conduit means 12 to a far or distal end 12' where it is connected to an introduction means generally indicated as 14. The introduction means includes an introduction cone or stoma cone 16 having one end connected to or disposed in direct fluid communication with the intestine or stoma 18. Typically and as generally represented in FIG. 1, the stoma 18 is secured to the abdominal wall 20 by means of an adaptive collar 22. A collection facility 24 may be provided to remove the evacuated fecal matter once the cone 16 is removed from its fluid introducing position as generally represented in FIG. 1.

An important feature of the present invention comprises a flow indicator means generally indicated as 26 and connected to the conduit means 12 so as to allow flow of irrigating liquid therethrough. The flow of irrigating liquid, to be explained in greater hereinafter, is accomplished through the flow indicator means 26 whether such direction of flow is from the supply container 10 towards the introduction means 14 and intestine 18 or in a reverse direction from the intestine 18 back towards the flow indicator means 26 such as when peristaltic action has been developed. The flow indicator means 26 comprises a first flow channel generally indicated as 28 and a second flow channel generally indicated as 30. Each of the flow channels 28 and 30 are more specifically defined by an elongated hollow interior tube 32 and 34 respectively. Correspondingly positioned opposite ends 32', 34' and 32", 34" are both interconnected to what may be referred to as common fluid junctions 36 and 38. Each of the common fluid junctions comprises a liquid receiving chamber 42 and 44 having one end as at 42' and 44' respectively connected in fluid communication with the conduit means 12 as at 12' and 12" respectively. In addition, each of the tubes 32 and 34 communicate with the liquid receiving chambers 42 and 44 at spaced apart relations to one another relative to the respective chambers 42 and 44. Due to the opposite ends 32', 34' and 32", 34" connected in fluid communication with a common receiving chamber 42 and 44 respectively, irrigating liquid will concurrently flow through tubes 32 and 34 defining the first and second flow channels 28 and 30 respectively.

Another important feature of the present invention is the provision of flow indicator means in the form of a first flow indicator 30' and a second flow indicator 52 respectively located on the interior of the first and second flow channels of 28 and 30.

The respective transverse dimensions of the indicator elements 30' and 52 relative to the tubes 32 and 34 in which they are mounted allows for the displacement or travel of the indicator elements 30' and 52 along with the irrigating liquid passing through the respective tubes 32 and 34 and in the same direction. Also, such relative dimensions between the indicator elements and the tubes in which they travel serves to provide a space therebetween to accomplish liquid flow therebeyond. Accordingly, liquid entering, for example, the common junction 38 through the conduit means 12" will flow concurrently into both of the first and second flow channels 28 and 30, beyond the respective indicator elements 30' and 52 and out through conduit means 12', 12 through common junction 36.

Figure 2:
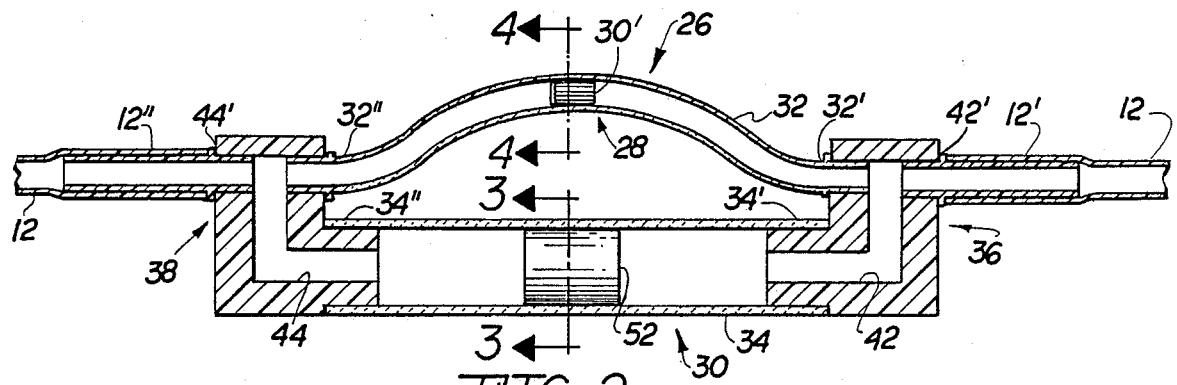
FIG. 2 is a sectional view in partial cutaway along line 2—2 showing interior details of the monitoring facility of the present invention.
Figure 3:
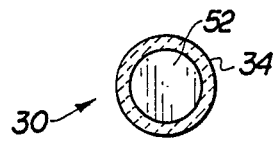
FIG. 3 is a sectional view taken along line 3—3 of FIG. 2 showing structural details of a second indicator element of the present invention.
Figure 4:
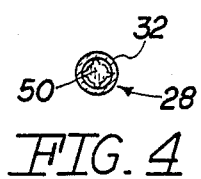
FIG. 4 is a sectional view along line 4—4 of FIG. 2 indicating structural details of an indicator associated with the monitoring facility of FIGS. 1 and 2.

Versatility of the flow indicator means is provided as follows: The first flow channel 28 is smaller preferably in cross-section than the second flow channel 30. The indicator element 30' has a specific gravity of about 1 and may be composed of a plug of medical grade plastic. In a preferred construction, the inside diameter of the tube 32 is about 3/16 of an inch and there is a diametrical clearance between this plug and the inside diameter of the tube of about 0.017 inch, that is, relatively small. As shown, the transverse dimension of the tube 32 is significantly less than the transverse dimension of the tube 34, the latter being about 7/16 of an inch inside diameter while the diameter of the plug 52 is about 0.370 inch and has a somewhat larger specific gravity than the earlier mentioned plug and of about 1.11 to 1.25 inch. Accordingly, the response to pressure of the flow of liquid through the tube 32 will be noticeably greater and more rapid than the rate of response to pressure change of the flow through the tube 34 provided that both of the correspondingly positioned opposite ends 32', 34', and 32", 34", are exposed to the same flow pressure when liquid passes through the respective junctions 36 and 38 into the flow channels 28 and 30, dependent upon the direction of liquid flow in conduit means 12. This of course is assured due to the fact that correspondingly positioned opposite ends of the flow channels 28 and 30 communicate directly with the common liquid receiving chambers 42 and 44 as shown in FIG. 2.

Based on the above it should be readily apparent that the indicator element 30' will be displaced upon the development of even a minimal amount of peristaltic action within the intestine 18. Upon the development of peristaltic action in the intestine 18 a back flow of irrigating liquid will be developed due to the pressure of the peristaltic action created within the intestine 18. This back flow will cause a reverse flow of direction of the irrigating liquid from the intestine 18 through the conduit means 12 into the flow indicating means 26 through conduit 12, 12' (see FIG. 2) and into the common junction 36. A minimal back flow of irrigating liquid due to the creation of minimal amount of peristaltic action within the intestine 18 will be quickly "detected" causing the beginning of displacement of the indicator element 30' within the tube 32. While such minimal amount of peristaltic action will not immediately displace the indicator element 52 within tube 34 to the extent of rapid displacement of the indicator element 30' within tube 32 due to the difference in characteristics, set forth above, in the second flow channel 30 the indicator element 52 within tube 34 will also be displaced following initiation of the peristaltic action. Accordingly in the aforementioned and defined "weak" patients flow of irrigating fluid from the supply container 10 through the conduit means 12 can be stopped by a flow regulating means 70 upon the development of even a minimal amount of peristaltic action indicated by adequate displacement of the "more sensitive" indicator element 30' relative to the displacement of the "normal" indicator element 52 as they travel respectively in their tubes 32 and 34 defining the respective first and second flow channel 28 and 30. The existence of the second flow channel 30 however allows use of the flow indicator means 26 for "normal" patients who commonly and consistently develop the "normal" amount of peristaltic action in the intestine 18.

Now that the invention has been described,

What is claimed is:

1. An apparatus for controlled intestinal irrigation comprising:
   A. a container means for supply and storage of irrigating liquid,
   B. introduction means positionable adjacent to and in fluid delivering relation with an entrance to an intestine being irrigated for introducing liquid thereto,
   C. conduit means disposed in interconnecting and fluid communicating relation between said container means and said introduction means,
   D. flow regulating means connected to said conduit means and structured and disposed to regulate liquid flow from said container means to said introduction means, whereby flow of irrigating liquid to the intestine may be selectively stopped by said flow regulating means upon an indication of peristaltic action of the intestine,
   E. a flow indicator means for indicating direction of flow within said conduit means and connected to said conduit means between said container means and said introduction means,
   F. said flow indicator means comprising a first flow channel and a second low channel means connected in fluid receiving relation to said conduit and relatively disposed to define two substantially parallel paths of liquid flow between said conduit means and said introduction means, G. said flow indicator means further comprising a first indicator element of a specific gravity of about 1 and a second indicator element of a specific gravity of greater than 1.1 movably disposed within said first and second flow channels respectively and within liquid flow passing therethrough, H. said first flow channel having a transverse dimension substantially less than said second flow channel and responding more rapidly to pressure change of the liquid flow therealong, I. each of said flow indicator elements cooperatively disposed and structured relative to said respective flow channels and in which they are mounted for responsive displacement therein based on peristaltic action of the intestine during flow of liquid through said respective flow channels, and J. said first indicator element displaceable with liquid flow along the length of said first flow channel in a direction from said introduction means to said container means at a more rapid response rate than displacement of said second indicator element along said second flow channel.

2. A system an in claim 1 wherein said first and said second flow channels each comprise an elongated tube terminating at correspondingly positioned opposite ends, said opposite ends interconnected in fluid communication to one another and to said conduit at common junctions, whereby liquid is passable concurrently into and out of each of said correspondingly positioned opposite ends of said tubes through said respectively positioned junctions.

3. A system as in claim 2 wherein said first and said second indicator elements each comprise a transverse dimension sufficiently smaller than said respective tube in which they are mounted to define a space therebetween, said space being dimensioned sufficient to allow passage of liquid along said space in bypassing relation to said respective indicator elements as liquid flow passes along said respective flow channel.

4. A system as in claim 3 wherein said first indicator element has a smaller transverse dimension than said second indicator element in the same proportion as said elongated tube of said tube and second flow channels.

5. A system as in claim 2 wherein at least one of said elongated tubes of said first and second flow channels are substantially transparent along at least a portion of their length, said indicator element within said one tube being viewable therein.

6. A system as in claim 5 wherein each of said elongated tubes of said first and said second flow channels are transparent along at least a portion of the length thereof, displacement of each of said indicator elements along the length of said respective tubes being viewable therethrough.

7. A system as in claim 2 wherein said tube of said first flow channel comprises a great longitudinal dimension than said tube of said second flow channel.

8. An assembly as in claim 7 wherein said tube of said first flow channel comprises a curvilinear longitudinal configuration and said tube of said second flow channel comprises a substantially linear longitudinal configuration.

9. A system as in claim 2 wherein each of said common junctions comprise a liquid receiving chamber disposed and configured for interconnection and fluid communication with said conduit means and correspondingly positioned opposite ends of eaach of said tubes of said first and second flow channels, said opposite ends of said tubes connected to a same common junction being disposed in spaced apart relation to one another.

10. A system as in claim 9 wherein said opposite end of said tube of said first flow channel is secured to said liquid receiving chamber upstream of said opposite end of said tube of said second flow channel at one of said common junctions receiving liquid from said conduit means and directing it into said flow indicator means.

11. A system as in claim 10 wherein said opposite ends of said second flow channel is secured to said liquid receiving chamber downstream of said opposite end of said tube of said first flow channel at one of said common junctions receiving liquid from said conduit means and directing it into said flow indicator means.

12. A system as in claim 9 wherein said second flow channel has a greater transverse dimension than said liquid receiving chamber and is disposed and at an opposite end thereof relative to said conduit means.

13. A system as in claim 2 wherein opposite ends of said tube of said first flow channel are structured and disposed to restrict displacement of said respective indicator element therebeyond and out of said tube.

14. A system as in claim 2 wherein at least one of said tubes comprises graduated markings extending along the length thereof and viewable from an exterior thereof, whereby degree of displacement of at least one of the indicator elements along said one tube is determinable by relative positions of said one indicator element is said graduated markings.

* * * * *